US009632048B2

United States Patent
Shu et al.

(10) Patent No.: US 9,632,048 B2
(45) Date of Patent: Apr. 25, 2017

(54) SHEET RESISTANCE MEASURING METHOD

(71) Applicant: BOE TECHNOLOGY GROUP CO., LTD., Beijing (CN)

(72) Inventors: Shi Shu, Beijing (CN); Bing Sun, Beijing (CN); Bin Zhang, Beijing (CN); Kexin Lu, Beijing (CN); Yue Shi, Beijing (CN); Zhijun Lv, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 279 days.

(21) Appl. No.: 14/470,902

(22) Filed: Aug. 27, 2014

(65) Prior Publication Data

US 2015/0260670 A1 Sep. 17, 2015

(30) Foreign Application Priority Data

Mar. 14, 2014 (CN) .......................... 2014 1 0096391

(51) Int. Cl.
*G01N 27/04* (2006.01)
*G01R 27/00* (2006.01)

(52) U.S. Cl.
CPC ........... *G01N 27/041* (2013.01); *G01R 27/00* (2013.01)

(58) Field of Classification Search
CPC ......... G01N 27/02–27/24; G01R 27/00–27/32
See application file for complete search history.

(56) References Cited

U.S. PATENT DOCUMENTS

| 5,247,262 | A | 9/1993 | Cresswell et al. |
| 5,691,648 | A * | 11/1997 | Cheng ...................... G01B 7/06 324/715 |
| 6,537,708 | B2 | 3/2003 | Chan |
| 2005/0112544 | A1* | 5/2005 | Xu ......................... C12M 23/12 435/4 |
| 2005/0255715 | A1* | 11/2005 | Cheng ................. H01L 51/0009 438/795 |

(Continued)

FOREIGN PATENT DOCUMENTS

| CN | 102539919 | 7/2012 |
| CN | 102621390 | 8/2012 |

(Continued)

OTHER PUBLICATIONS

Chinese Office Action with English Language Translation, dated Dec. 22, 2015, Chinese Application No. 201410096391.1.

(Continued)

*Primary Examiner* — Huy Q Phan
*Assistant Examiner* — David Frederiksen
(74) *Attorney, Agent, or Firm* — Blakely Sokoloff Taylor & Zafman LLP

(57) ABSTRACT

The present disclosure relates to a sheet resistance measuring method, comprising the following steps: connecting at least one to-be-measured thin film having a predetermined shape to two separate electrodes in at least one pair of electrodes; measuring the resistance between the two electrodes in each pair of electrodes; and determining the sheet resistance of the to-be-measured thin film based on the measured resistance and the shape of the corresponding to-be-measured thin film.

8 Claims, 4 Drawing Sheets

(56) References Cited

U.S. PATENT DOCUMENTS

| | | | | |
|---|---|---|---|---|
| 2008/0143354 | A1* | 6/2008 | Chen | G01R 31/2648 324/715 |
| 2009/0001351 | A1* | 1/2009 | Shibasaki | G01R 33/06 257/14 |
| 2010/0156840 | A1* | 6/2010 | Frey | G06F 3/044 345/174 |
| 2010/0166614 | A1* | 7/2010 | Uchiyama | G01N 27/12 422/98 |
| 2011/0317741 | A1* | 12/2011 | Seefeld | G01D 3/0365 374/185 |
| 2012/0212242 | A1* | 8/2012 | Masel | G01N 27/127 324/693 |
| 2014/0062845 | A1* | 3/2014 | Brahma | G09G 3/006 345/92 |
| 2014/0159705 | A1* | 6/2014 | Fujiwara | G01R 1/06755 324/149 |

FOREIGN PATENT DOCUMENTS

| | | |
|---|---|---|
| CN | 103063921 | 4/2013 |
| CN | 103235185 | 8/2013 |

OTHER PUBLICATIONS

Chinese Office Action with English Language Translation, dated Jun. 7, 2016, Chinese Application No. 201410096391.1.

* cited by examiner

SHEET RESISTANCE MEASURING METHOD

FIELD OF THE DISCLOSURE

The present disclosure relates to the field of sheet resistance measurement, and particularly to a sheet resistance measuring method.

BACKGROUND OF THE DISCLOSURE

Nano carbon materials such as carbon nano tube, Fullerene and graphene are used to manufacture transparent conductive thin film. In mass production, detection needs to be effectively performed for the sheet resistance thereof. Since the conductive thin film made of a nano carbon material such as carbon nano tube, Fullerene or graphene is very thin, generally only 0.35 nm or so, a conventional four probe method cannot be used to measure the sheet resistance thereof, and instead, a non-contact type sheet resistance measuring apparatus needs to be used. However, the non-contact type sheet resistance measuring apparatus increases the detection cost. Besides, nano carbon materials such as carbon nano tube, Fullerene and graphene are generally subjected to patterning treatment in mass production, it is necessary to evaluate whether the sheet resistance having undergone the patterning treatment is affected. Therefore, it is desirable to provide a method of rapidly and accurately measuring the sheet resistance of the conductive thin film made of the nano carbon material.

SUMMARY OF THE DISCLOSURE

The present disclosure meets the above needs by providing a sheet resistance measuring method, the method comprising:
  connecting at least one to-be-measured thin film having a predetermined shape to two separate electrodes in at least one pair of electrodes, wherein the two electrodes in each pair of electrodes are connected by a corresponding one of the at least one to-be-measured thin film, and wherein the length of an edge of each of the two electrodes on the side connected to the to-be-measured thin film is not less than the width of the to-be-measured thin film at the end connected to the electrode;
  measuring the resistance between the two electrodes of said each pair of electrodes; and
  determining the sheet resistance of the to-be-measured thin film based on the measured resistance and the shape of the corresponding to-be-measured thin film.

To make the present disclosure apparent and illustrate how it is implemented, the present disclosure will be described now with reference to the following figures by way of examples.

DETAILED DESCRIPTION OF PREFERRED EMBODIMENTS

Embodiments of the present disclosure are based on the following principle: connecting a to-be-measured thin film material to two separate electrodes, and measuring the resistance between the two electrodes, and then determining the sheet resistance of the to-be-measured thin film material through a certain conversion relationship, wherein the sheet resistance of the conductive thin film made of a nano carbon material such as carbon nano tube. Fullerene or graphene can be measured rapidly without using a non-contact type measuring apparatus.

Figure 1:
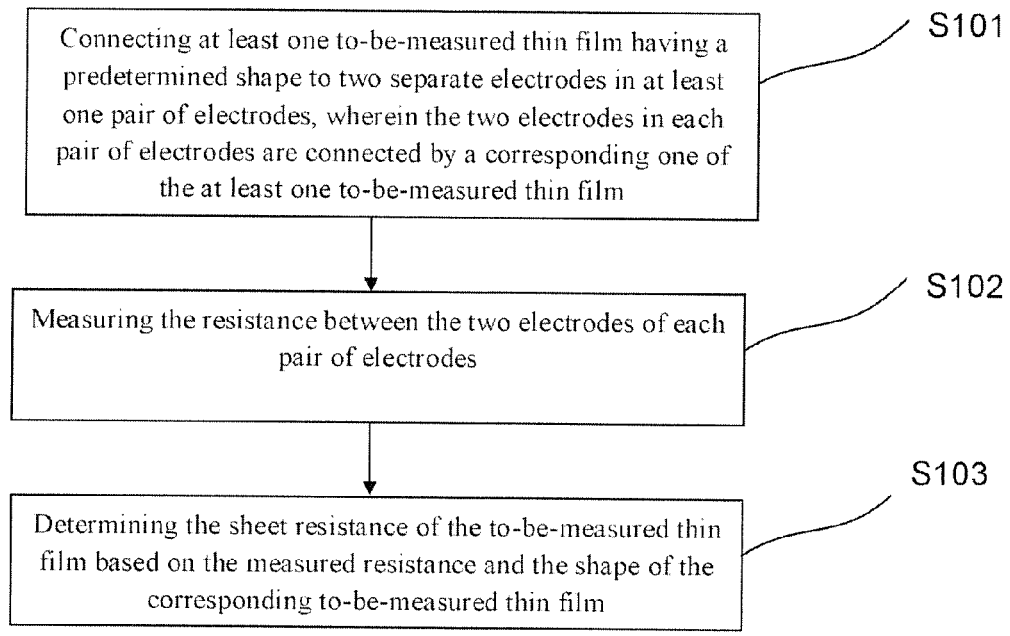
FIG. 1 is a flow chart of a sheet resistance measuring method according to an embodiment of the present disclosure.

FIG. 1 is a flow chart of a sheet resistance measuring method according to an embodiment of the present disclosure. As shown in FIG. 1, the method comprises the following steps:

Step S101: connecting at least one to-be-measured thin film having a predetermined shape to two separate electrodes in at least one pair of electrodes, wherein the two electrodes in each pair of electrodes are connected by a corresponding one of the at least one to-be-measured thin film;

Step S102: measuring the resistance between the two electrodes of each pair of electrodes. The resistance between the two electrodes in the present embodiment may be measured in any current resistance measuring manner;

Step S103: determining the sheet resistance of the to-be-measured thin film based on the resistance between the two electrodes of each pair of electrodes and the shape of the corresponding to-be-measured thin film.

Hereunder, graphene is taken as an example for illustration purpose. In step S101, a graphene thin film may be formed in a manner for example transfer printing, and a predetermined number of graphene thin films having a predetermined shape may be obtained by patterning treatment such as photoetching or cutting. The shape of the graphene thin film may be either regular or irregular.

Besides, the electrodes may be formed on a base plate of a substrate in a manner such as magnetron sputtering or vacuum evaporation, and may be made of a metal or alloy.

Figure 2:
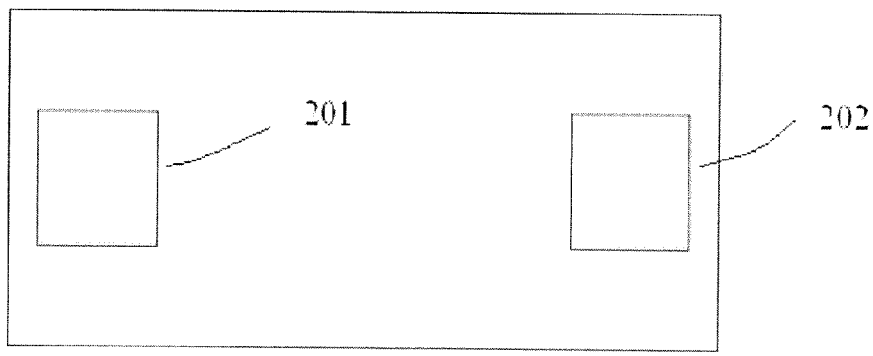
FIG. 2 is a schematic view of a pair of electrodes according to an embodiment of the present disclosure.

FIG. 2 is a schematic view of a pair of electrodes according to an embodiment of the present disclosure. The two electrodes 201, 202 in each pair of electrodes are separate from each other. The shape of each electrode may be square as shown in FIG. 2 or rectangular (not shown) to prevent the electrode's resistance from exerting an influence on precision of sheet resistance measurement.

Figure 3:
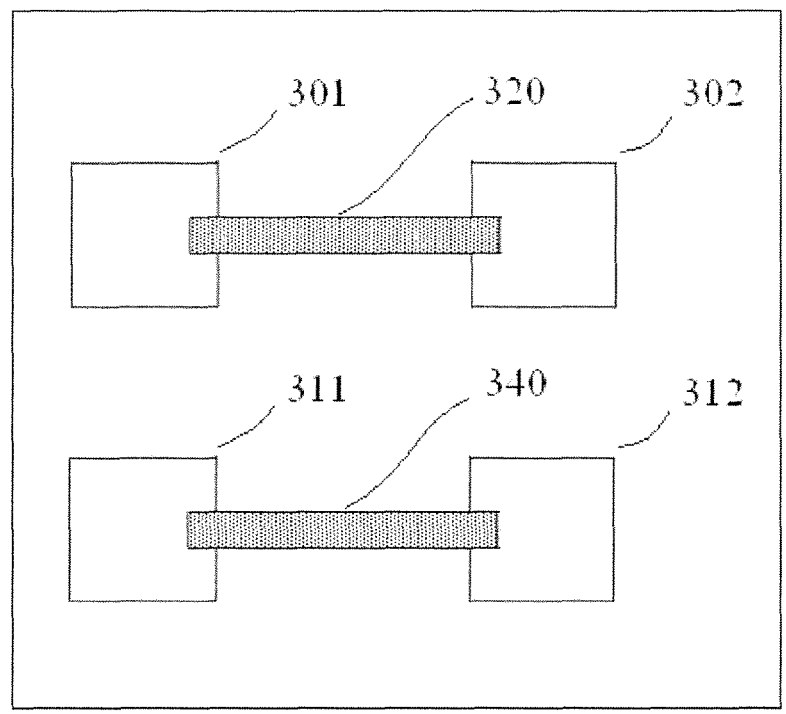
FIG. 3 is a schematic view of connecting two electrodes in a pair of electrodes by using a to-be-measured thin film according to an embodiment of the present disclosure.

FIG. 3 is a schematic view of connecting two electrodes by using the to-be-measured thin film according to an embodiment of the present disclosure, wherein two graphene thin films 320, 340 having a predetermined shape are used to respectively connect two separate electrodes 301 and 302, 311 and 312 in two pairs of electrodes. To ensure the accuracy of measurement, the length of an edge of each of the two electrodes on the side connected to the graphene thin film should not be less than the width of the graphene thin film at the end connected to the electrode. For example, the length of an edge of the electrode 301 on the side connected to the graphene thin film 320 is greater than the width of the graphene thin film 320 at the end connected to the electrode 301. Besides, two pairs of electrodes are shown in FIG. 3 only for illustration purpose. It should be appreciated that more pairs of electrodes are feasible.

In addition, in step S102, the resistance between the two electrodes may be measured in any current resistance measuring manner. The sheet resistance of the to-be-measured thin film connecting the two electrodes may be obtained through certain calculations (discussed below) by using the measured resistance between the two electrodes.

Figure 4A:
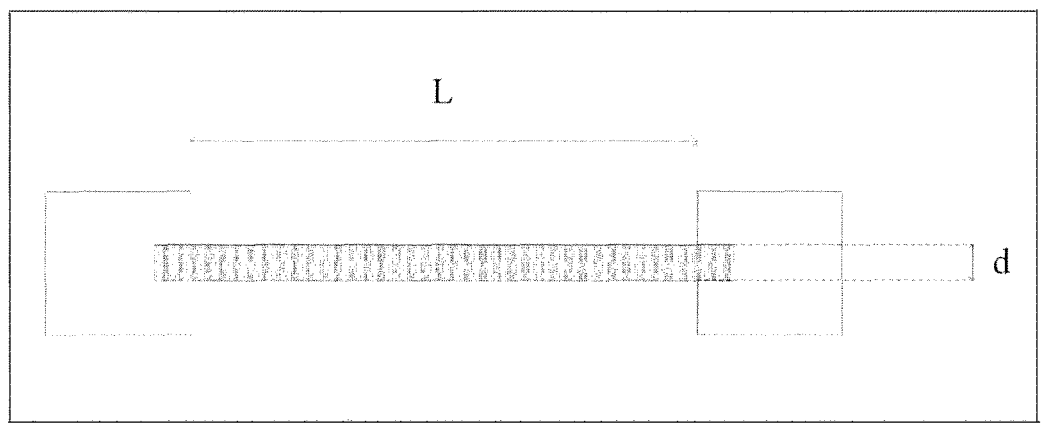
FIG. 4A-FIG. 4C are schematic views of different arrangements of the electrodes and the to-be-measured thin film according to an embodiment of the present disclosure.

Besides, in step S103, to simplify calculation, the shape of the to-be-measured thin film may be configured as a regular geometrical shape having a predetermined length and width, as shown in FIG. 4A.

In this case, the sheet resistance of the to-be-measured thin film may be determined in the following manner:

First, a corresponding sheet resistance is determined based on the resistance between the two electrodes in each pair of electrodes according to the following equation:

$$Rs_i = R_i \cdot d_i / L_i$$

Wherein $Rs_i$ is the sheet resistance determined based on the $i^{th}$ pair of electrodes, $R_i$ is resistance measured between the two electrodes in the $i^{th}$ pair of electrodes, $d_i$ is the width of the to-be-measured thin film connecting the $i^{th}$ pair of electrodes, and $L_i$ is the length of the to-be-measured thin film between the two electrodes in the $i^{th}$ pair of electrodes.

Then, arithmetic averaging is performed for the determined respective sheet resistances $$Rs_{avg} = 1/N \cdot \sum_{i=1}^{N} Rs_i,$$

and the resulted average value $Rs_{avg}$ is regarded as the sheet resistance of the to-be-measured thin film, wherein N is the number of the pair of the at least one pair of electrodes, and N≥1 and is an integer.

Further, if only one pair of electrodes is used (namely, N=1), optionally the resistance between the pair of electrodes may be measured for multiple times over a period of time, and a corresponding sheet resistance is determined based on the resistance measured each time and the shape of the to-be-measured thin film, and then arithmetic averaging is performed for the determined respective sheet resistances, and the resultant average value is regarded as the sheet resistance of the to-be-measured thin film.

Figure 4B:
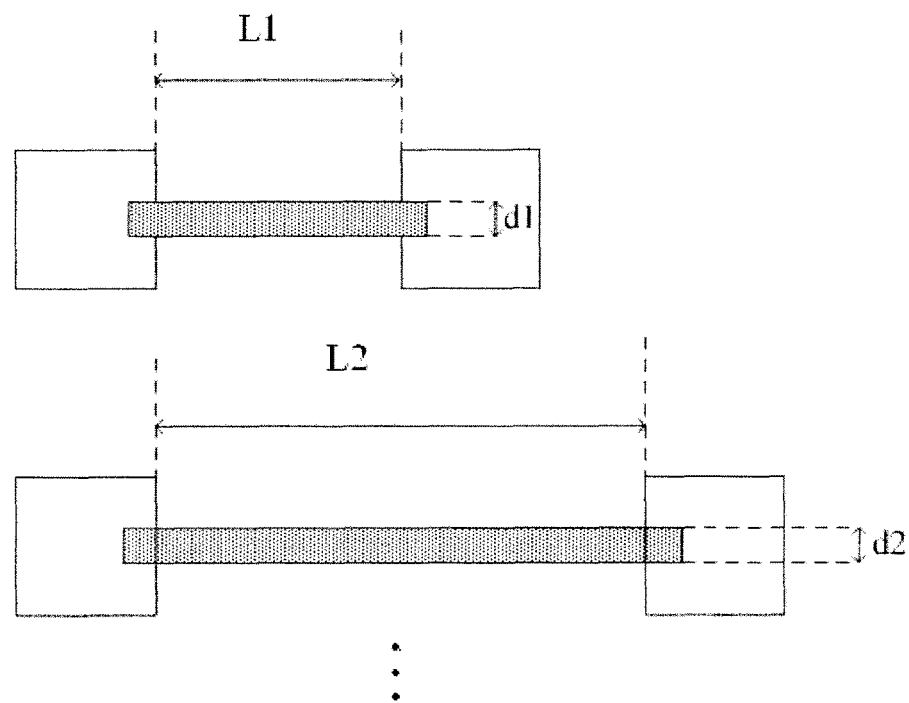

Alternatively, as shown in FIG. 4B, if at least two pair of electrodes (N≥2) are used and the lengths of the to-be-measured thin films between two electrodes in the at least two pairs of electrodes are unequal, the sheet resistance of the to-be-measured thin film may be measured in the following manner:

First, according to the equation $$Rs = \frac{|R_i - R_j|}{|L_i - L_j|} \cdot |d_i - d_j|,$$

a corresponding sheet resistance is determined based on resistances between the two electrodes of every two pairs of electrodes, wherein Rs is the sheet resistance determined based on every two pairs of electrodes, $R_i$ is the resistance measured between the two electrodes in the pair of electrodes, $d_i$ is the width of the to-be-measured thin film connecting the $i^{th}$ pair of electrodes, and $L_i$ is the length of the to-be-measured thin film between the two electrodes in the pair of electrodes; $R_j$ is the resistance measured between the two electrodes in the $j^{th}$ pair of electrodes, $d_j$ is the width of the to-be-measured thin film connecting the $j^{th}$ pair of electrodes, and $L_j$ is the length of the to-be-measured thin film between the two electrodes in the $j^{th}$ pair of electrodes, wherein 1≤i, j≤N, i≠j, N is the number of the pair of the at least one pair of electrodes, and N≥2 and is an integer.

Then, arithmetic averaging is performed for the determined respective sheet resistances, and the resultant average value is regarded as the sheet resistance of the to-be-measured thin film.

Figure 4C:
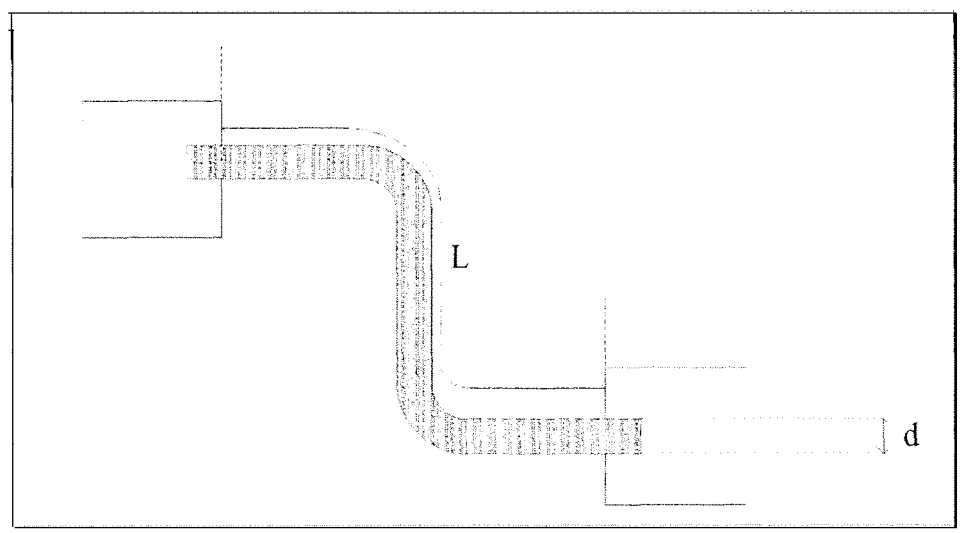

It is to be noted that while the embodiments above are described taking the shape of the to-be-measured thin film shown in FIG. 4A and FIG. 4B for example, the shape of the to-be-determined thin film is not limited to the shape shown in FIG. 4A and FIG. 4B, and may be designed in a shape for example as shown in FIG. 4C depending on actual application scenarios. In the case that the to-be-measured thin film is in an irregular shape, parameters of the shape of the to-be-measured thin film may be determined according to the actual situation, and the sheet resistance of the to-be-measured thin film may be determined in a resistance calculating manner suitable for the irregular shape.

Additionally, in an embodiment of the present disclosure, after connecting the to-be-measured thin film to the two electrodes, a protective layer may be formed on the electrodes and the to-be-measured thin film to protect the electrodes and the to-be-measured thin film from oxidization reaction or collision which causes the sheet resistance of the to-be-measured material to change and thereby affects the measurement precision.

Figure 5:
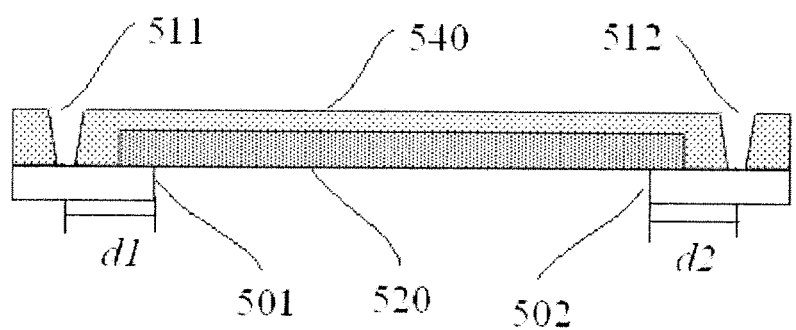
FIG. 5 is a schematic view of covering the electrodes and the to-be-measured thin film with a protective layer and providing a via according to an embodiment of the present disclosure.

FIG. 5 is a schematic view of covering the electrodes and the to-be-measured thin film with a protective layer and providing a via according to an embodiment of the present disclosure, wherein a protective layer 540 covers electrodes 501, 502 and a to-be-measured thin film 520.

Specifically, the method may comprises the following step:

A. forming the protective layer covering the electrodes and the to-be-measured thin film.

The protective layer 540 may be made of either an organic material or an inorganic material. In case of an organic material, an organic protective layer may be formed by a process including for example gluing, exposure, development and postbaking; In case of an inorganic material, an inorganic protective layer may be formed by a process including for example film-forming, gluing, exposure, development, etching and glass.

B. subjecting the protective layer to a via process at positions of the electrodes to respectively form vias 511, 512 to expose the corresponding electrodes.

The vias 511 and 512 ensure that the corresponding electrodes 501 and 502 are exposed so that the resistance between the two electrodes 501, 502 is measured through the vias. The vias exposing the respective electrodes may be sized the same, and distances between the respective vias and an edge on the side of the electrodes connected with the to-be-measured thin film may be equal. For example, the distance d1 between the via 511 and an edge on the side of the corresponding electrode 501 connected with the to-be-measured thin film 520 is equal to the distance d2 between the via 512 and an edge on the side of the electrode 502 connected with the to-be-measured thin film 520. In fact, when a contact resistance between the electrodes and the to-be-measured thin film is smaller, the positions of the vias may be flexibly selected due to a smaller measurement error.

In the embodiments of the disclosure, the electrodes may be made of a metal such as gold, platinum or silver so that the contact resistance between the electrodes and the to-be-measured thin film is small and thereby the measurement error is reduced. Alternatively, in order to cut the cost, the electrodes may be made of a metallic material such as molybdenum, aluminum, neodymium, copper or a metal alloy. Particularly in application scenarios of manufacturing display panels, these metallic materials are easily available, and the electrodes may be formed by advantageously using a synchronization process involved in the display panel manufacture procedure.

The sheet resistance manufacturing method according to the present disclosure may be used for large-scale detection of patterned conductive thin films to quickly detect the sheet resistance of the to-be-measured thin film in the process flow and consequently find abnormal situations in time.

The invention claimed is:

1. A sheet resistance measuring method, comprising the following steps:
   connecting two separate electrodes of each of at least one pair of electrodes using a corresponding one of at least one to-be-measured thin film having a predetermined shape, wherein an edge of each electrode where the corresponding to-be-measured thin film is connected has a length not less than a width of a connected end of the corresponding to-be-measured thin film where the electrode is connected;
   measuring a resistance between the two electrodes of each of the at least one pair of electrodes; and
   determining the sheet resistance of the to-be-measured thin film based on the measured resistance and the shape of the corresponding to-be-measured thin film,
   wherein after the step of connecting the two separate electrodes of each of the at least one pair of electrodes, the method further comprises forming a protective layer covering the electrodes and the to-be-measured thin film, and subjecting the protective layer to a via process at positions of the electrodes to respectively form vias to expose the respective electrodes, and
   wherein the step of measuring the resistance between the two electrodes of each of the at least one pair of electrodes comprises measuring the resistance between the two electrodes of each pair of electrodes through the vias.

2. The method according to claim 1, wherein the vias are sized the same, and distances between the vias and the edges of the respective electrodes where the to-be-measured thin film is connected are equal.

3. The method according to claim 1, wherein the at least one pair of electrodes comprises one pair of electrodes,
   wherein the step of measuring the resistance between the two electrodes of each of the at least one pair of electrodes comprises
   measuring the resistance between the two electrodes in the pair of electrodes for multiple times over a period of time, and
   wherein the step of determining the sheet resistance of the to-be-measured thin film based on the measured resistance and the shape of the corresponding to-be-measured thin film comprises
   determining a corresponding sheet resistance based on the resistance measured each time and the shape of the to-be-measured thin film, performing arithmetic averaging for the determined respective sheet resistances, and regarding a resultant average value as the sheet resistance of the to-be-measured thin film.

4. The method according to claim 1, wherein the predetermined shape is a regular geometrical shape having a predetermined length and width, and
   wherein the step of determining the sheet resistance of the to-be-measured thin film based on the measured resistance and the shape of the corresponding to-be-measured thin film comprises
   determining a corresponding sheet resistance based on the resistance between the two electrodes in each pair of electrodes according to the equation $Rs_i = R_i \cdot d_i / L_i$,
   performing arithmetic averaging $$Rs_{avg} = 1/N \sum_{i=1}^{N} Rs_i$$

for the determined respective sheet resistances, and regarding a resultant average value $Rs_{avg}$ as the sheet resistance of the to-be-measured thin film,
   wherein $Rs_i$ is the sheet resistance determined based on the $i^{th}$ pair of electrodes, $R_i$ is the resistance measured between the two electrodes in the $i^{th}$ pair of electrodes, $d_i$ is the width of the to-be-measured thin film connecting the $i^{th}$ pair of electrodes, $L_i$ a length of a portion of the to-be-measured thin film between the two electrodes in the $i^{th}$ pair of electrodes, N is the number of the pair of the at least one pair of electrodes, and $N \geq 1$ and is an integer.

5. The method according to claim 4, wherein the electrodes are made of gold, platinum or silver.

6. The method according to claim 1, wherein the predetermined shape is a regular geometrical shape having a predetermined length and width, and lengths of the to-be-measured thin films between the two electrodes in respective pairs of electrodes are unequal, and
   wherein the step of determining the sheet resistance of the to-be-measured thin film based on the measured resistance and the shape of the corresponding to-be-measured thin film comprises
   determining a corresponding sheet resistance based on resistances between the two electrodes of every two pairs of electrodes according to the equation $$Rs = \frac{|R_i - R_j|}{|L_i - L_j|} \cdot |d_i - d_j|,$$

performing arithmetic averaging for the determined respective sheet resistances, and regarding a resultant average value as the sheet resistance of the to-be-measured thin film,
   wherein Rs is the sheet resistance determined based on every two pairs of electrodes, $R_i$ is the resistance measured between the two electrodes in the $i^{th}$ pair of electrodes, $d_i$ is the width of the to-be-measured thin film connecting the $i^{th}$ pair of electrodes, and $L_i$ is a length of a portion of the to-be-measured thin film between the two electrodes in the $i^{th}$ pair of electrodes; $R_j$ is the resistance measured between the two electrodes in the $j^{th}$ pair of electrodes, $d_j$ is the width of the to-be-measured thin film connecting the $j^{th}$ pair of electrodes, and $L_j$ is a length of a portion of the to-be-measured thin film between the two electrodes in the $j^{th}$ pair of electrodes, wherein $1 \le i$, $j \le N$, $i \ne j$, N is the number of the pair of the at least one pair of electrodes, and $N \ge 2$ and is an integer.

7. The method according to claim 6, wherein the electrodes are made of molybdenum, aluminum, neodymium, copper or a metal alloy.

8. The method according to claim 1, wherein the to-be-measured thin film is a nano carbon material thin film.

\* \* \* \* \*

UNITED STATES PATENT AND TRADEMARK OFFICE
CERTIFICATE OF CORRECTION

PATENT NO. : 9,632,048 B2
APPLICATION NO. : 14/470902
DATED : April 25, 2017
INVENTOR(S) : Shi Shu et al.

Page 1 of 1

It is certified that error appears in the above-identified patent and that said Letters Patent is hereby corrected as shown below:

In the Claims

Column 6, Claim 4, Line 29, please delete "a length" and insert --is a length--.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*